(12) United States Patent
Watanabe et al.

(10) Patent No.: US 11,325,116 B2
(45) Date of Patent: May 10, 2022

(54) TIP SET

(71) Applicant: EIKEN KAGAKU KABUSHIKI KAISHA, Tokyo (JP)

(72) Inventors: Hidetoshi Watanabe, Tochigi (JP); Fumihiko Kazumi, Tokyo (JP); Yuji Segawa, Tochigi (JP)

(73) Assignee: EIKEN KAGAKU KABUSHIKI KAISHA, Tokyo (JP)

( * ) Notice: Subject to any disclaimer, the term of this patent is extended or adjusted under 35 U.S.C. 154(b) by 141 days.

(21) Appl. No.: 16/766,262

(22) PCT Filed: Nov. 14, 2018

(86) PCT No.: PCT/JP2018/042159
§ 371 (c)(1),
(2) Date: May 21, 2020

(87) PCT Pub. No.: WO2019/107155
PCT Pub. Date: Jun. 6, 2019

(65) Prior Publication Data
US 2020/0368738 A1 Nov. 26, 2020

(30) Foreign Application Priority Data
Nov. 29, 2017 (JP) .............................. JP2017-228903

(51) Int. Cl.
*B01L 3/02* (2006.01)
*B67B 7/00* (2006.01)
*C12N 15/10* (2006.01)

(52) U.S. Cl.
CPC .............. *B01L 3/0275* (2013.01); *B67B 7/24* (2013.01); *B01L 2200/141* (2013.01); *B01L 2300/048* (2013.01); *B01L 2300/0672* (2013.01)

(58) Field of Classification Search
None
See application file for complete search history.

(56) References Cited

U.S. PATENT DOCUMENTS

2006/0171851 A1* 8/2006 Motadel ................ B01L 3/0241
422/400
2016/0332156 A1* 11/2016 Tajima ............... G01N 35/1079

FOREIGN PATENT DOCUMENTS

EP 1685901 A1 8/2016
JP H8-320274 A 12/1996
(Continued)

OTHER PUBLICATIONS

Patent Cooperation Treaty, International Search Report for PCT/JP2018/042159, dated Jan. 15, 2019, pp. 1-2.

*Primary Examiner* — Matthew D Krcha
*Assistant Examiner* — Brittany I Fisher
(74) *Attorney, Agent, or Firm* — Pillsbury Winthrop Shaw Pittman LLP

(57) ABSTRACT

Provided is a tip set used for a genetic testing device. The tip set includes a piercing tip breaking a lid portion of a reagent container filled with a reagent to open the reagent container and an injection tip injecting a sample solution containing a target gene nucleic acid into a microchip. The injection tip has a reservoir storing the sample solution in an internal space and an injection needle protruding from the reservoir, an opening the internal space to a side opposite to the injection needle is formed in the reservoir, and the piercing tip has a fitting portion fitted to the injection tip to connect the injection tip and the piercing tip.

6 Claims, 23 Drawing Sheets

(56) References Cited

FOREIGN PATENT DOCUMENTS

| | | |
|---|---|---|
| JP | 2012-159337 A | 8/2012 |
| JP | 2013-542849 A | 11/2013 |
| WO | 2010/140680 A1 | 12/2010 |
| WO | 2012/040333 A1 | 3/2012 |
| WO | 2013/076998 A1 | 5/2013 |
| WO | 2015/108164 A1 | 7/2015 |

\* cited by examiner

TIP SET

RELATED PATENT APPLICATIONS

This application is based on and claims the benefit of priority from International Application No. PCT/JP2018/042159, filed on Nov. 14, 2018, which claims priority to Japanese Patent Application No. 2017-228903, filed on Nov. 29, 2017, 2017, the contents of which are hereby incorporated by reference in their entirety.

TECHNICAL FIELD

The present invention relates to a tip set used for a genetic testing device.

BACKGROUND ART

In recent years, genetic tests using the polymerase chain reaction (PCR) method, the loop-mediated isothermal amplification (LAMP) method, and the like have been performed. Genetic testing is configured by an extraction and purification step of extracting and purifying a target gene nucleic acid from a specimen, an amplification step of amplifying the nucleic acid extracted and purified in the extraction and purification step, and a detection step of detecting the nucleic acid amplified in the amplification step. It should be noted that the extraction and purification step is also referred to as pretreatment for genetic testing.

Set in a genetic testing device during such genetic testing are a reaction tube in which a specimen and an extract are injected, a reagent cartridge in which a plurality of reagent containers are filled with pretreatment reagents (hereinafter, simply referred to as "reagents"), and a microchip in which a reaction reagent for reacting (amplifying) with a target gene nucleic acid is enclosed in a plurality of wells. Further, the reagent cartridge stores a piercing tip opening the reagent container by breaking the lid portion of the reagent container, a pipette tip dispensing the reagent with which the reagent container is filled to the reaction tube, and an injection tip injecting a sample solution into the microchip with the target gene nucleic acid extracted and purified in the reaction tube (see, for example, Patent Literature 1).

Further, the above-described genetic testing is performed by the piercing tip, the pipette tip, and the injection tip mounted on a pipette head of the genetic testing device being moved in the up-down and horizontal directions. Specifically, the reagent container is opened first by the piercing tip breaking the lid portion of the reagent container. Next, the reagent with which the reagent container is filled is dispensed into the reaction tube by the pipette tip and a sample solution from which the target gene nucleic acid has been extracted and purified is prepared. Next, the sample solution is dripped into the injection tip by the pipette tip and the sample solution is stored at the injection tip. Next, the sample solution is injected into the microchip by the injection tip, mixed with the sample solution, and incubated at a predetermined temperature. The nucleic acid is amplified as a result. Next, the amplified nucleic acid is detected by the presence or absence of an amplification product being confirmed in the microchip.

CITATION LIST

Patent Literature

Patent Literature 1: International Publication No. 2010/140680

SUMMARY OF INVENTION

Technical Problem

The injection tip includes an injection needle injecting the sample solution into the microchip and a tubular reservoir storing the sample solution. Further, an opening for dripping the sample solution into the reservoir and mounting the pipette head is formed at a position of the reservoir on the side that is opposite to the injection needle. Accordingly, when the injection tip is mounted on the pipette head and moved in the horizontal direction, the liquid surface of the sample solution stored in the reservoir may fluctuate and the sample solution may adhere to the pipette head. The sample solution adhesion to the pipette head may result in contamination of different sample solutions.

In this regard, an object of the present invention is to provide a tip set capable of preventing contamination of a sample solution.

Solution to Problem

A tip set according to one aspect of the present invention is a tip set used for a genetic testing device. The tip set includes a piercing tip breaking a lid portion of a reagent container filled with a reagent to open the reagent container and an injection tip injecting a sample solution containing a target gene nucleic acid into a microchip. The injection tip has a reservoir storing the sample solution in an internal space and an injection needle protruding from the reservoir, an opening opening the internal space to a side opposite to the injection needle is formed in the reservoir, and the piercing tip has a fitting portion fitted to the injection tip to connect the injection tip and the piercing tip.

In this tip set, the injection tip and the piercing tip are connected by the fitting portion of the piercing tip being fitted to the injection tip. Accordingly, it is possible to mount the injection tip onto a pipette head via the piercing tip by mounting the piercing tip connected to the injection tip onto the pipette head. As a result, the injection tip and the pipette head do not come into direct contact with each other, and thus sample solution adhesion to the pipette head attributable to fluctuation of the liquid surface of the sample solution is suppressed. As a result, contamination of the sample solution can be prevented.

The piercing tip may have an insertion portion inserted into the reservoir from the opening, and the fitting portion may be fitted to the injection tip when the insertion portion is inserted in the reservoir. In this tip set, it is possible to block at least a part of the opening by means of the piercing tip by inserting the insertion portion of the piercing tip into the reservoir from the opening of the injection tip. Further, the injection tip and the piercing tip are connected with at least a part of the opening blocked by the piercing tip by the fitting portion of the piercing tip being fitted to the injection tip. Accordingly, it is possible to suppress sample solution leakage from the reservoir. As a result, contamination of the sample solution can be further prevented.

The fitting portion may be a protrusion protruding from an outer peripheral surface of the insertion portion, and the protrusion may be pressed against an inner peripheral surface of the reservoir when the insertion portion is inserted in the reservoir. In this tip set, the fitting portion is the protrusion protruding from the outer peripheral surface of the insertion portion, and the protrusion is pressed against the inner peripheral surface of the reservoir when the insertion portion is inserted in the reservoir. Accordingly, it is possible to easily connect the injection tip and the piercing tip simply by inserting the insertion portion of the piercing tip into the reservoir. In addition, since the protrusion is pressed against the inner peripheral surface of the reservoir, the connection precision and the fitting strength of the injection tip and the piercing tip are improved.

At least one of the piercing tip and the injection tip may further have an air vent allowing the internal space of the reservoir to be ventilated from an outside in a state where the injection tip and the piercing tip are connected. It becomes difficult to inject the sample solution from the injection needle into the microchip due to the internal pressure of the reservoir when the opening of the injection tip is completely blocked by the piercing tip. In a case where the sample solution is suctioned into the microchip from the injection needle by the negative pressure in the microchip, in particular, the effect of the internal pressure of the reservoir becomes extremely large. In this tip set, the air vent allows the internal space of the reservoir to be ventilated from the outside in a state where the injection tip and the piercing tip are connected, and thus the effect of the internal pressure of the reservoir during sample solution injection from the injection needle into the microchip can be reduced. Accordingly, it is possible to appropriately inject the sample solution from the injection needle into the microchip even in a case where the insertion portion is inserted in the reservoir from the opening and the injection tip and the piercing tip are connected.

The air vent may be a groove formed in an outer peripheral surface of the piercing tip. In this tip set, the groove formed in the outer peripheral surface of the piercing tip communicates with the internal space of the reservoir, and thus the internal space of the reservoir can be opened to the atmosphere when the injection tip and the piercing tip are connected. As a result, an increase in the internal pressure of the internal space is eliminated and it is possible to prevent the reagent solution from leaking out from the injection needle in connecting the injection tip and the piercing tip. Further, the effect of the internal pressure of the reservoir during sample solution injection from the injection needle into the microchip can be extremely reduced.

The piercing tip may have a step portion against which an end surface of the reservoir on the opening side abuts, and the groove may also be formed in the step portion. In this tip set, the end surface of the reservoir that is on the opening side abuts against the step portion of the piercing tip, and thus it is possible to restrict the amount of insertion of the piercing tip with respect to the reservoir. As a result, when the injection tip is mounted on the pipette head via the piercing tip, the position of the injection tip in the up-down direction can be positioned with high precision. In addition, since the groove of the air vent is also formed in the step portion, the internal space of the reservoir can be opened to the atmosphere even when the end surface of the reservoir on the opening side abuts against the step portion of the piercing tip.

The piercing tip may have a blade portion having a sharp tip, and the blade portion may have a plurality of blades radially extending and having a blade edge forming a polygonal pyramid ridgeline. In this tip set, the piercing tip has the blade portion having a sharp tip, and thus the lid portion of the reagent container can be broken by the blade portion. Further, since the blade portion has the plurality of blades that radially extend and have a blade edge forming a polygonal pyramid ridgeline, the pressure by which the lid portion of the reagent container is broken is more concentrated than in a case where the blade portion is formed in a simple cone or polygonal pyramid. Accordingly, it is possible to break the lid portion of the reagent container with a smaller pressurizing force.

Advantageous Effects of Invention

According to the present invention, contamination of a sample solution can be prevented.

DETAILED DESCRIPTION OF EMBODIMENTS

Figure 1:
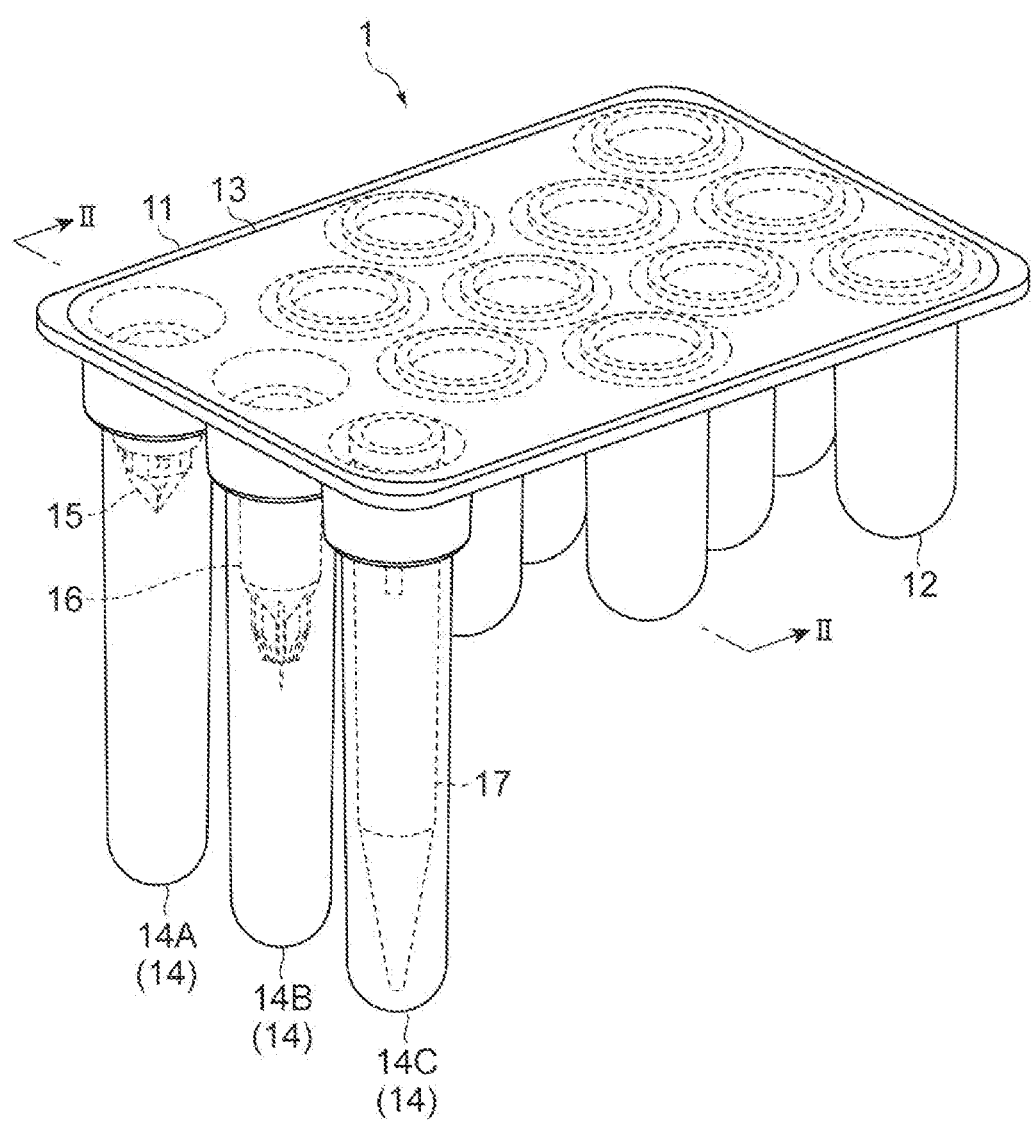
FIG. 1 is a perspective view illustrating a reagent cartridge.

Hereinafter, an embodiment of a tip set according to one aspect of the present invention will be described with reference to the drawings. The tip set according to the embodiment is a tip set that is set in a genetic testing device performing a genetic test. It should be noted that the same or corresponding elements are denoted by the same reference numerals in the drawings and redundant description will be omitted.

[Genetic Testing Device]

The genetic testing device in which the tip set according to the present embodiment is set is a device performing a genetic test. Set in this genetic testing device are a reaction tube in which a specimen and an extract are injected, a reagent cartridge in which a plurality of reagent containers are filled with reagents, and a microchip in which a reagent (reaction reagent) for reacting (amplifying) with a target gene nucleic acid is enclosed.

In the genetic test using this genetic testing device, first, each reagent with which a reagent cartridge 1 is filled is dispensed into the reaction tube to prepare a sample solution in which a target gene nucleic acid is extracted and purified (extraction and purification step). Next, the sample solution is injected into the microchip, the sample solution is mixed with the sample solution, and the nucleic acid is amplified by incubation at a predetermined temperature (amplification step). Next, the nucleic acid amplified in the amplification step is detected by the presence or absence of an amplification product being confirmed in the microchip (detection step).

[Reagent Cartridge]

Figure 2:
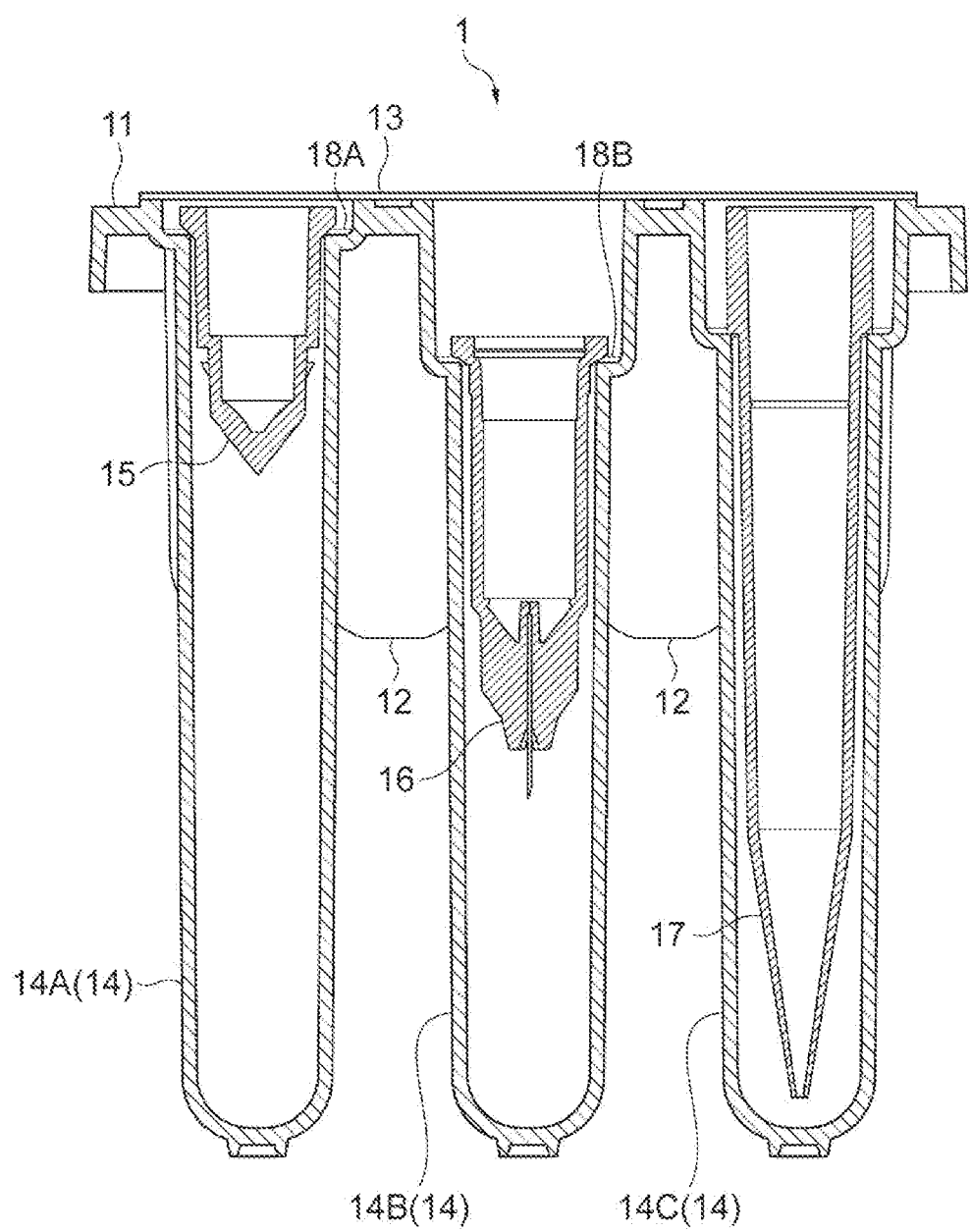
FIG. 2 is a cross-sectional view taken along line II-II illustrated in FIG. 1.

As illustrated in FIGS. 1 and 2, the reagent cartridge 1 includes a cartridge main body 11, a plurality of reagent containers 12 filled with reagents (pretreatment reagents), a lid portion 13 for sealing the reagents with which the reagent containers 12 are filled, and a plurality of storage wells 14 in which various tips are stored.

Each reagent container 12 may be provided integrally with the cartridge main body 11 or may be detachably provided on the cartridge main body 11.

The lid portion 13 seals the reagent with which the reagent container 12 is filled by sealing the opening formed at the upper end of the reagent container 12. The lid portion 13 may seal each reagent container 12 individually or may seal some or all of the reagent containers 12 together. The lid portion 13 is formed of, for example, an aluminum laminated film.

The reagent cartridge 1 includes a first storage well 14A, a second storage well 14B, and a third storage well 14C as the storage wells 14. Stored in the first storage well 14A is a piercing tip 15 opening the reagent container 12 by breaking the lid portion 13 of the reagent container 12. Stored in the second storage well 14B is an injection tip 16 injecting a sample solution into a microchip 2 with the target gene nucleic acid extracted and purified in the reaction tube. Stored in the third storage well 14C is a pipette tip 17 dispensing the reagent with which the reagent container 12 is filled into the reaction tube. The piercing tip 15 and the injection tip 16 are the tip set according to the present embodiment. It should be noted that the up-down direction of the piercing tip 15 and the injection tip 16 in the following description is an up-down direction in a state where the piercing tip 15 and the injection tip 16 are stored in the first storage well 14A and the second storage well 14B.

[Microchip]

Figure 14:
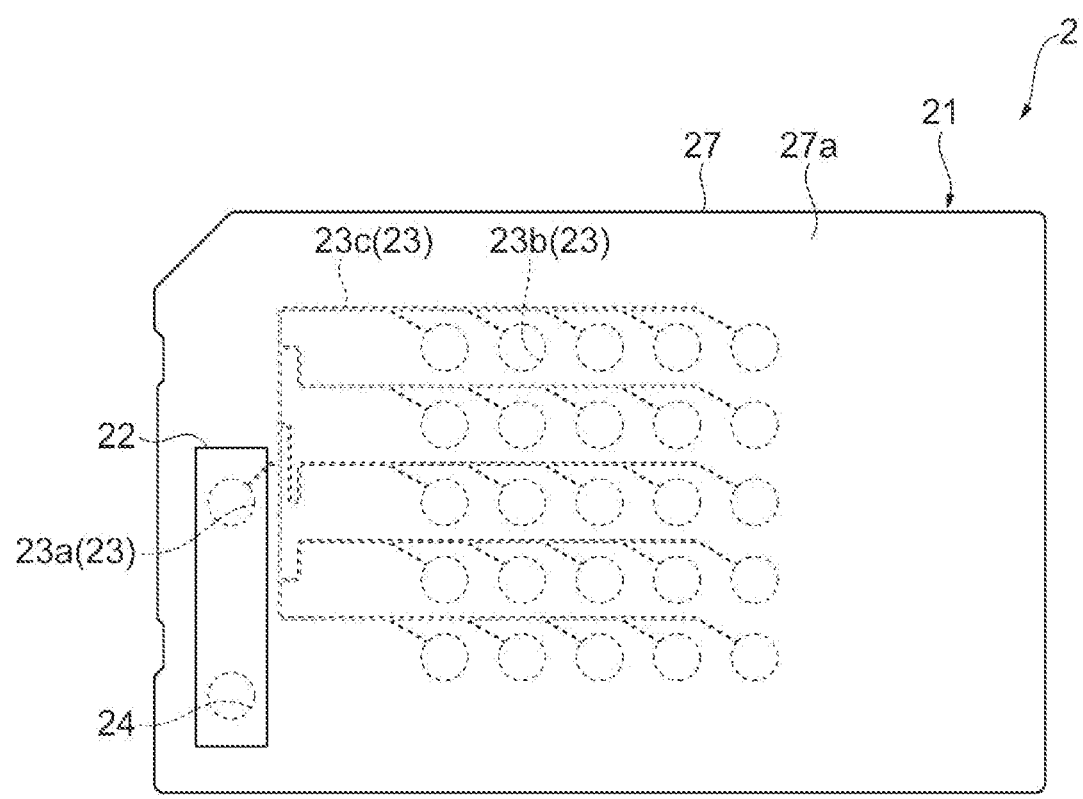
FIG. 14 is a plan view illustrating a microchip.
Figure 15:
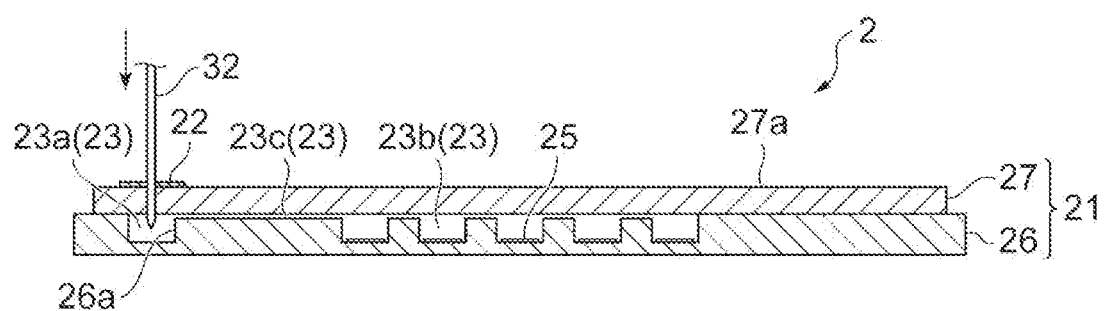
FIG. 15 is a schematic cross-sectional view of the microchip.
Figure 16:
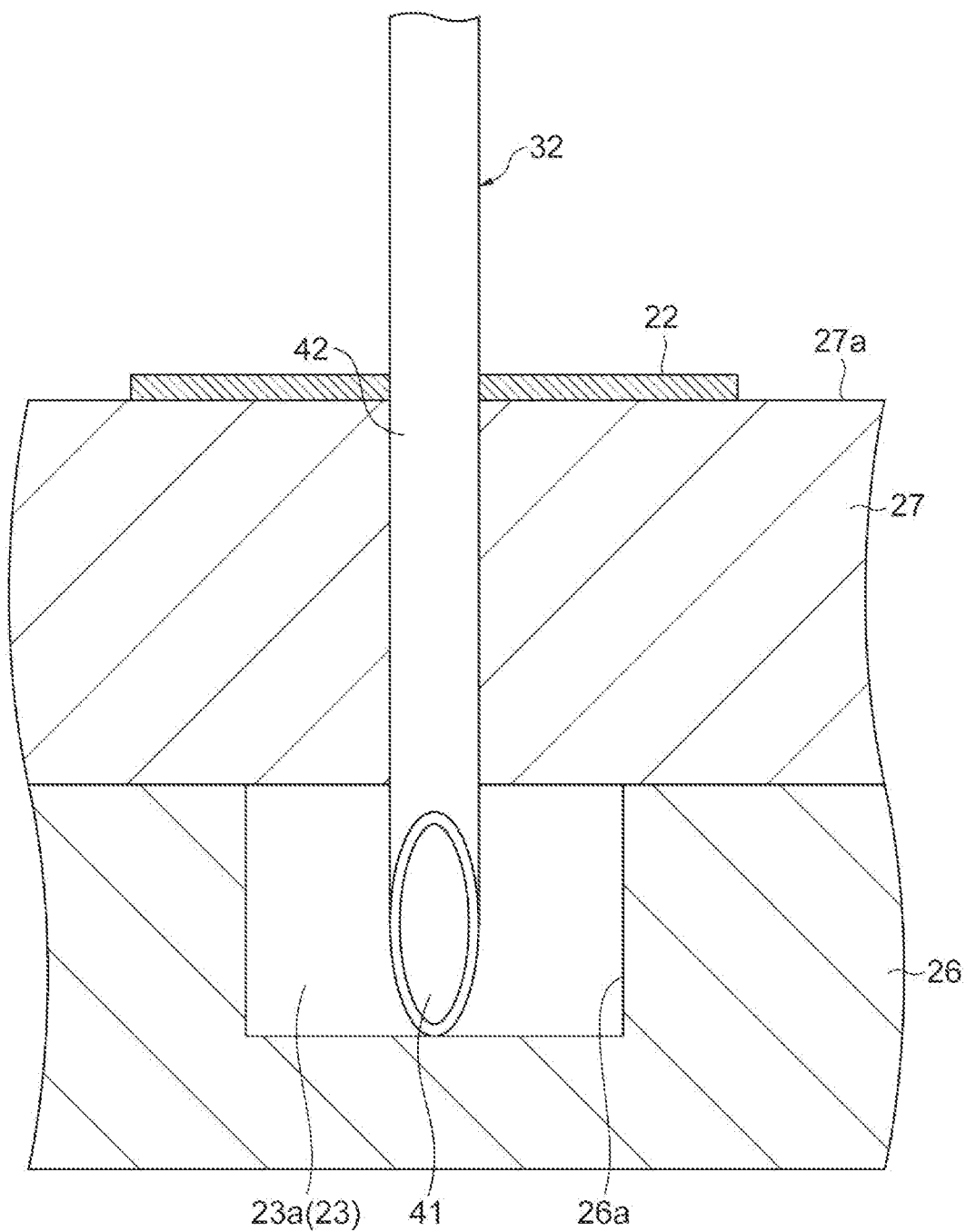
FIG. 16 is a schematic cross-sectional view illustrating a state where a reaction space is punctured by an injection needle.

As illustrated in FIGS. 14 and 15, the microchip 2 includes a transparent chip main body 21 and a transparent reinforcing film 22 as described in, for example, Japanese Unexamined Patent Publication No. 2017-067595.

A reaction space 23 and a confirmation space 24, which are independent of each other, are formed in the chip main body 21. The reaction space 23 and the confirmation space 24 are closed spaces formed in the microchip 2. The pressure in the reaction space 23 and the confirmation space 24 is reduced with respect to the atmospheric pressure and can be reduced to, for example, 1/100 atm or less. The reaction space 23 has an injection space 23a into which a sample solution is puncture-injected, a plurality of reagent-enclosed spaces 23b enclosing a reagent 25 for reacting with the sample solution to be injected, and a flow path 23c allowing the injection space 23a and each reagent-enclosed space 23b to communicate with each other. In the present embodiment, a reagent corresponding to the nucleic acid contained in the sample solution is used as the reagent 25. The confirmation space 24 encloses, for example, a color changing agent (not illustrated) that changes color when the sample solution is mixed.

The chip main body 21 is formed in a thin and substantially rectangular plate shape. The chip main body 21 is a two-layer structure of a first plate-shaped portion 26 and a second plate-shaped portion 27 laminated on one surface of the first plate-shaped portion 26. The first plate-shaped portion 26 and the second plate-shaped portion 27 are joined in a state where the first plate-shaped portion 26 and the second plate-shaped portion 27 overlap each other.

The first plate-shaped portion 26 is formed in a thin and substantially rectangular plate shape. Formed on the surface of the first plate-shaped portion 26 that is on the second plate-shaped portion 27 side are a reaction space recess 26a for forming the reaction space 23 and a confirmation space recess (not illustrated) for forming the confirmation space 24.

The first plate-shaped portion 26 has gas impermeability. The material of the first plate-shaped portion 26 is not particularly limited, and gas-impermeable glass, synthetic resin, or the like can be used as the material. Examples of the synthetic resin include polymethyl methacrylate (PMMA: acrylic resin), polycarbonate (PC), polystyrene (PS), polyethylene terephthalate (PET), COP, and cyclic polyolefin (COC).

The second plate-shaped portion 27 is formed in a thin and substantially rectangular plate shape. The second plate-shaped portion 27 forms the injection space 23a, the plurality of reagent-enclosed spaces 23b, and the flow path 23c of the reaction space 23 between the second plate-shaped portion 27 and the first plate-shaped portion 26 by covering the reaction space recess 26a. In addition, the second plate-shaped portion 27 forms the confirmation space 24 between the second plate-shaped portion 27 and the first plate-shaped portion 26 by covering the confirmation space recess.

The second plate-shaped portion 27 has a self-sealing property. The self-sealing property means that, even when a hole is formed by puncturing or the like, the hole is naturally sealed by a restoring force attributable to self-elastic deformation. Examples of the elastic material used for the second plate-shaped portion 27 include a silicone-based elastomer, an acrylic-based elastomer, a urethane-based elastomer, and a fluorine-based elastomer. It is preferable that the second plate-shaped portion further has gas permeability, and polydimethylsiloxane (PDMS) as a self-sealing and gas-permeable elastic material can be employed.

The reinforcing film 22 is attached to a surface 27a of the second plate-shaped portion 27, which is on the side opposite to the first plate-shaped portion 26. The reinforcing film 22 is attached to at least the position of the surface 27a of the second plate-shaped portion 27 that faces the injection space 23a and the confirmation space 24. The reinforcing film 22 is a transparent resin member formed in a thin film or tape shape. The reinforcing film 22 reinforces the surface 27a of the second plate-shaped portion 27 and suppresses deformation (maintains the shape) of the surface 27a of the second plate-shaped portion 27. Accordingly, it is preferable that the reinforcing film 22 is a film excellent in elasticity or a film excellent in shape retention.

The dimensions of the microchip 2 are not particularly limited. For example, the thickness of the first plate-shaped portion 26 is 2 mm, the thickness of the second plate-shaped portion 27 is 2 mm, the depth of the reaction space 23 and the confirmation space 24 is 1.5 mm, and the thickness of the reinforcing film 22 is 0.3 mm.

[Injection Tip]

Figure 3:
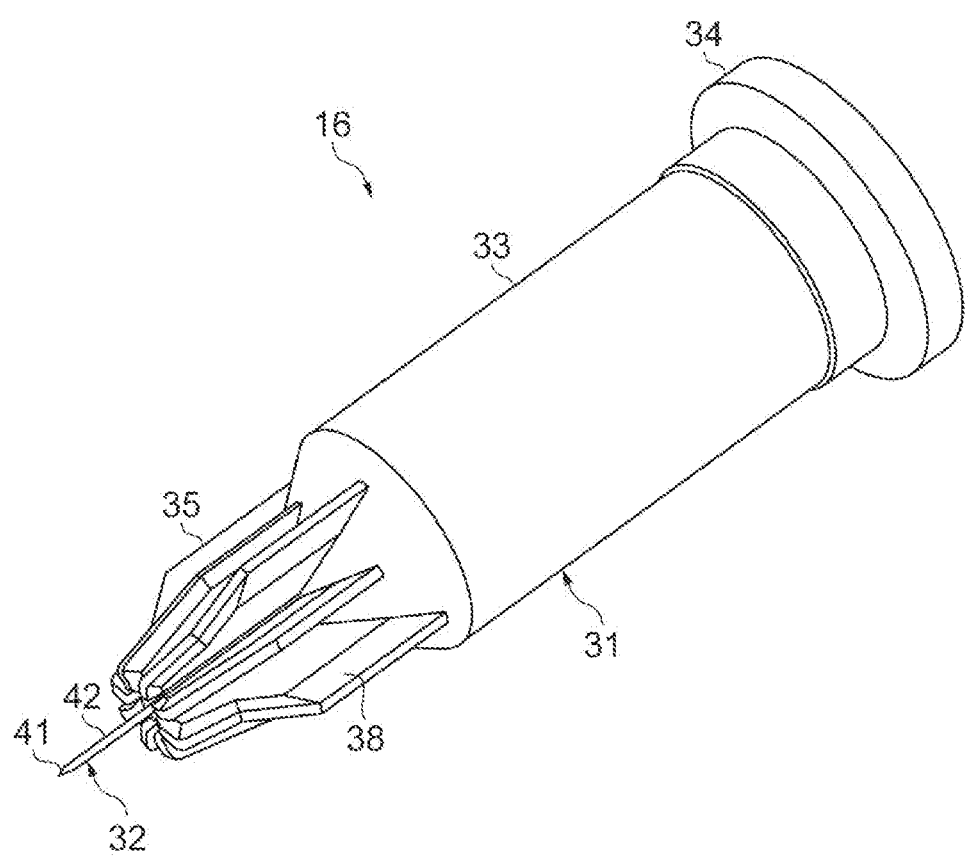
FIG. 3 is a perspective view illustrating an injection tip.
Figure 4A:
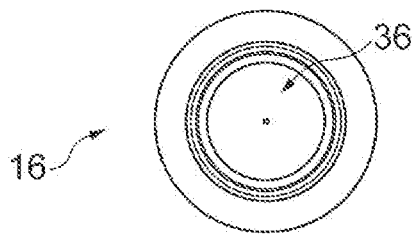
FIG. 4(a) is a plan view illustrating the injection tip.
Figure 4B:
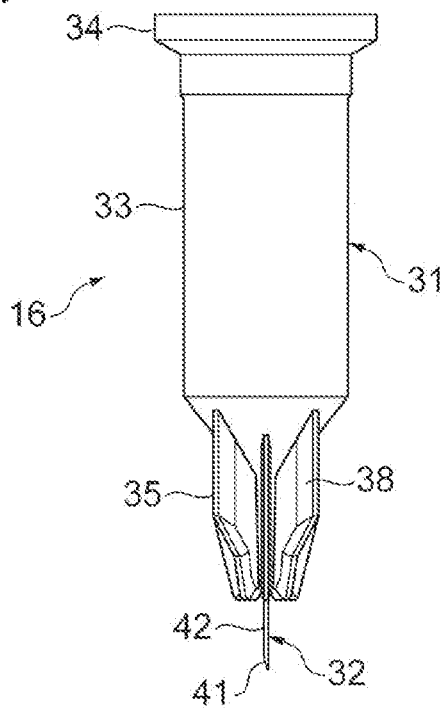
FIG. 4(b) is a front view illustrating the injection tip.
Figure 4C:
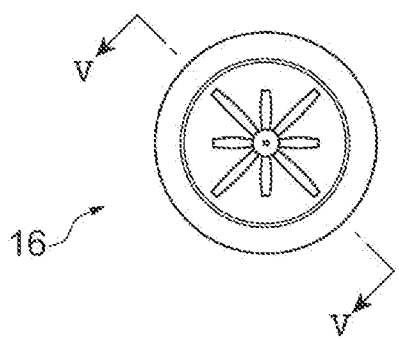
FIG. 4(c) is a bottom view illustrating the injection tip.
Figure 5:
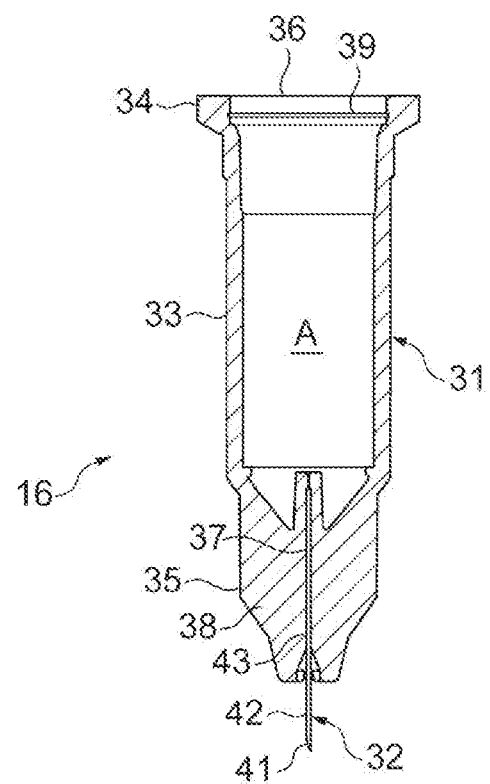
FIG. 5 is a cross-sectional view taken along line V-V illustrated in FIG. 4(c).
Figure 6:
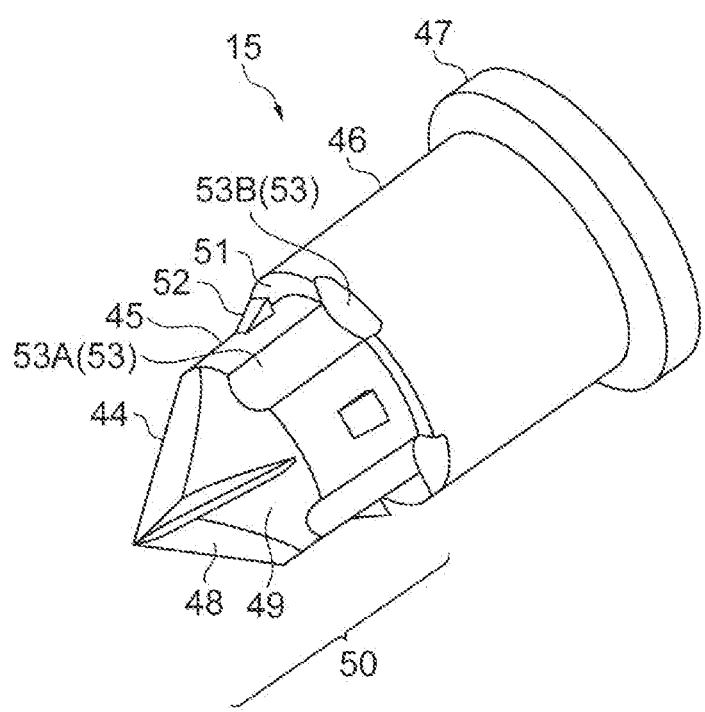
FIG. 6 is a perspective view illustrating a piercing tip.
Figure 7A:
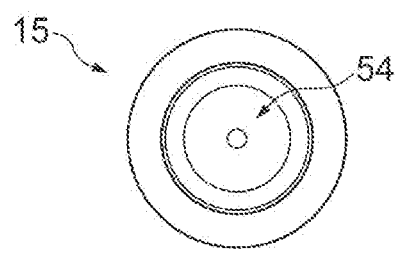
FIG. 7(a) is a plan view illustrating the piercing tip.
Figure 7B:
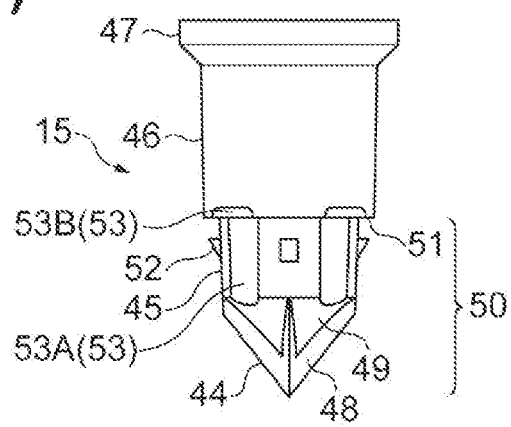
FIG. 7(b) is a front view illustrating the piercing tip.
Figure 7C:
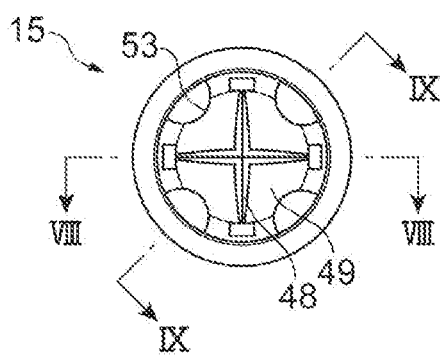
FIG. 7(c) is a bottom view illustrating the piercing tip.
Figure 8:
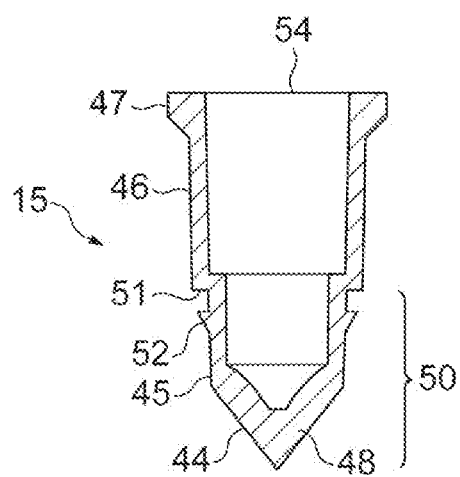
FIG. 8 is a cross-sectional view taken along line VIII-VIII illustrated in FIG. 7(c).
Figure 9:
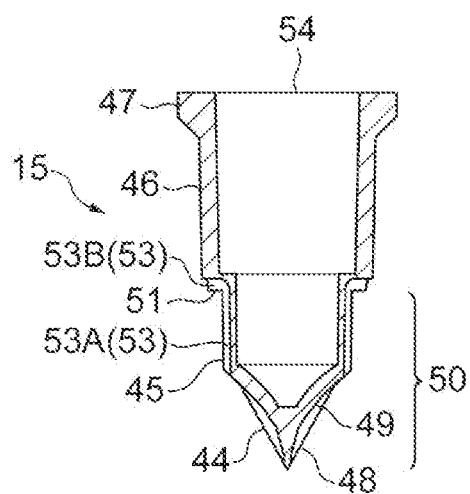
FIG. 9 is a cross-sectional view taken along line IX-IX illustrated in FIG. 7(c).
Figure 10:
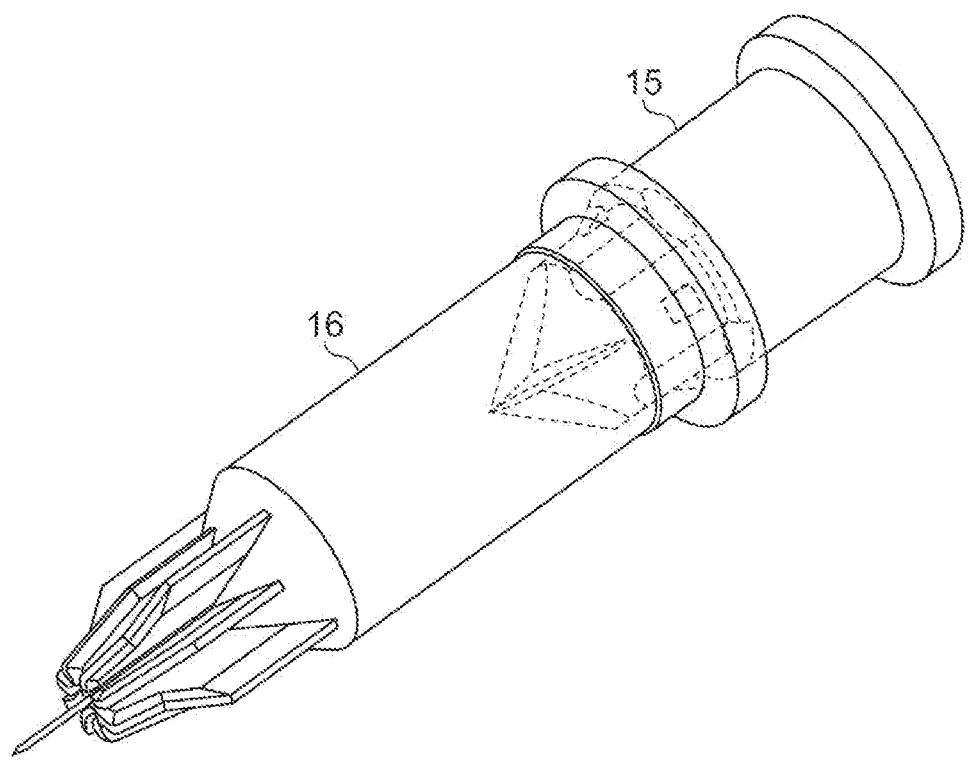
FIG. 10 is a perspective view illustrating a connected body of the injection tip and the piercing tip.
Figure 11:
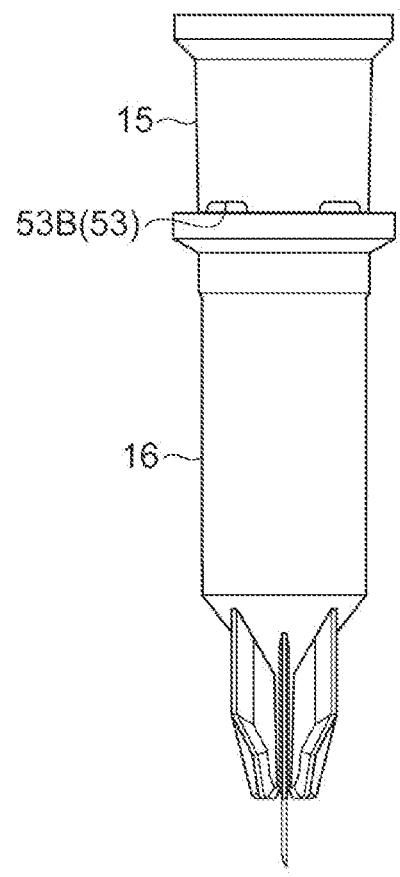
FIG. 11 is a front view of the connected body illustrated in FIG. 10.
Figure 12:
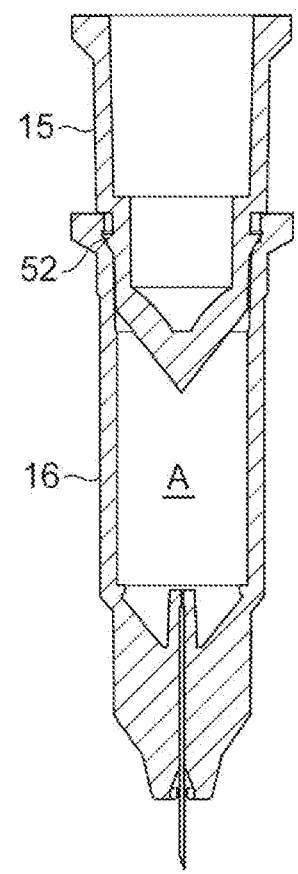
FIG. 12 is a cross-sectional view of the connected body illustrated in FIG. 10.
Figure 13:
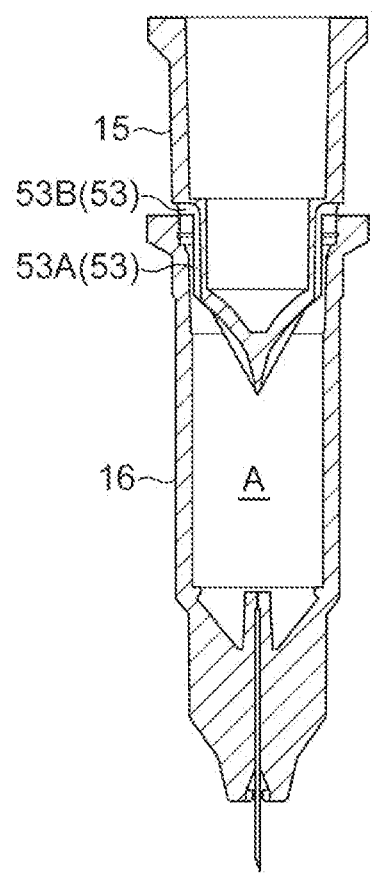
FIG. 13 is a cross-sectional view of the connected body illustrated in FIG. 10.

As illustrated in FIGS. 3 to 5, the injection tip 16 has a reservoir 31 storing a sample solution in an internal space A and an injection needle 32 protruding from the reservoir 31.

The reservoir 31 has a cylindrical portion 33, a flange portion 34, and a holding portion 35.

The cylindrical portion 33 is a part that forms the internal space A where the sample solution is stored. The cylindrical portion 33 is formed in a hollow cylindrical shape extending in the up-down direction, and the internal space A is formed on the inner peripheral surface side of the cylindrical portion 33. Formed at the upper end of the cylindrical portion 33 is an opening 36 that opens the internal space A upward (to the side opposite to the injection needle 32). The opening 36 is an opening for dripping the sample solution into the internal space A. In addition, the opening 36 is also an opening into which a pipette head 3 is inserted so that the injection tip 16 is mounted onto the pipette head 3 (see FIG. 20). In addition, as described later, the opening 36 is also an opening into which the piercing tip 15 is inserted so that the piercing tip 15 and the injection tip 16 are connected. A circumferential groove 39 is formed near the opening 36 in the inner peripheral surface of the cylindrical portion 33. The capacity of the reservoir 31, that is, the volume of the internal space A is not particularly limited. Preferably, the volume is larger than 135 µl. For example, the volume is approximately 200 µl.

As illustrated in FIGS. 2 to 5, the flange portion 34 is a part that is locked to the second storage well 14B. The flange portion 34 extends radially outward of the cylindrical portion 33 in the upper end portion of the cylindrical portion 33. Further, the flange portion 34 is locked by a step-shaped locking portion 18B formed in the second storage well 14B when the injection tip 16 is stored in the second storage well 14B of the reagent cartridge 1. The position of the locking portion 18B can be a position where the injection tip 16 does not reach the bottom surface of the second storage well 14B and the upper end of the injection tip 16 is sufficiently lower than the upper end of the second storage well 14B when the flange portion 34 is locked. In other words, in the second storage well 14B, a space is formed above the injection tip 16 stored in the second storage well 14B.

As illustrated in FIGS. 3 to 5, the holding portion 35 is a part where the injection needle 32 is held. The holding portion 35 is provided at the lower end of the cylindrical portion 33. A holding hole 37, where the injection needle 32 is held, is formed in the holding portion 35. The holding hole 37 extends in the up-down direction and communicates with the internal space A. In addition, a plurality of ribs 38 extending in the radial direction of the cylindrical portion 33 and the axial direction of the cylindrical portion 33 are formed in the holding portion 35. The rib 38 is formed in a plate shape. The lower ends (tips) of the plurality of ribs 38 are aligned, and the injection needle 32 protrudes downward from the lower ends of the plurality of ribs 38.

Polypropylene or the like can be used as the material of the reservoir 31, which is not particularly limited.

The injection needle 32 has a bevel 41, a needle tube 42, and a needle base 43. The bevel 41 is an obliquely cut part of the needle tip. The needle tube 42, which is a hollow metal tube continuing from the bevel 41, is a part protruding from the holding portion 35 (plurality of ribs 38) of the reservoir 31. The needle tube 42 is made of stainless steel according to the JIS standard. It should be noted that a lubricant such as silicone may be applied or coated on the outer peripheral surface of the needle tube 42. The needle base 43, which is a hollow metal tube continuing from the needle tube 42, is a part that is held by the holding portion 35 and does not protrude from the holding portion 35 (plurality of ribs 38) of the reservoir 31. The needle base 43 is held by the holding portion 35 by being inserted into the holding hole 37 of the holding portion 35. It should be noted that the injection tip 16 may include a needle sheath (not illustrated) covering the injection needle 32.

The dimensions of the injection needle 32 are not particularly limited. For example, the thickness of the injection needle 32 is 0.27 mm (31 G), the length of the injection needle 32 (total length of the bevel 41, the needle tube 42, and the needle base 43) is 3 mm, and the length of the bevel 41 is 0.7 mm.

As illustrated in FIGS. 3 to 5 and 16, the total length of the needle tube 42 and the bevel 41 is preferably longer than the thickness of the second plate-shaped portion 27 such that the tip of the injection needle 32 reaches the injection space 23a of the reaction space 23. In addition, the length of the bevel 41 is preferably shorter than the thickness of the second plate-shaped portion 27 such that the injection space 23a does not communicate with the outside when the sample solution is injected into the microchip 2. In addition, the total length of the needle tube 42 and the bevel 41 is preferably shorter than the length that is the sum of the thickness of the reinforcing film 22, the thickness of the second plate-shaped portion 27, and the depth of the injection space 23a such that the tip of the injection needle 32 does not hit the bottom surface of the injection space 23a. In a case where the microchip 2 does not include the reinforcing film 22 in this case, the total length of the needle tube 42 and the bevel 41 is preferably shorter than the length that is the sum of the thickness of the second plate-shaped portion 27 and the depth of the injection space 23a.

[Piercing Tip]

As illustrated in FIGS. 6 to 9, the piercing tip 15 has a blade portion 44, a first cylindrical portion 45, a second cylindrical portion 46, and a flange portion 47.

The blade portion 44 is a part that opens the reagent container 12 by breaking the lid portion 13 of the reagent container 12. The blade portion 44 is positioned in the lower end portion of the piercing tip 15 and has a sharp lower end. The blade portion 44 has a plurality of blades 48 that radially extend and have a blade edge forming a polygonal pyramid ridgeline. In other words, each blade 48 is formed in a thin plate shape (rib shape) that radially extends (in the radial direction of the first cylindrical portion 45) and the blade edge of the blade 48, which is the tip edge of the blade 48, forms a polygonal pyramid ridgeline. Further, a recess 49 recessed with respect to the blade edge of each blade 48 is between the blades 48 that are adjacent to each other. In other words, a circumscribed circle of the blade portion 44 is formed by the blade edge of each blade 48 and the recess 49 is formed at a position recessed from the circumscribed circle.

As illustrated in FIGS. 6 to 13, the first cylindrical portion 45 is a part that is inserted into the reservoir 31 from the opening 36 of the injection tip 16 together with the blade portion 44. Accordingly, the blade portion 44 and the first cylindrical portion 45 also function as an insertion portion 50 inserted into the reservoir 31. The first cylindrical portion 45 is connected to the upper end of the blade portion 44 and formed in a hollow cylindrical shape extending in the up-down direction. The outer diameter of the blade portion 44 is smaller than the inner diameter of the opening 36 of the injection tip 16. In addition, the maximum outer diameter of the blade portion 44 is also smaller than the inner diameter of the opening 36 of the injection tip 16.

The second cylindrical portion 46 is a part that is not inserted into the reservoir 31. The second cylindrical portion 46 is connected to the upper end of the first cylindrical portion 45 and formed in a hollow cylindrical shape extending in the up-down direction. The outer diameter of the second cylindrical portion 46 is larger than the inner diameter of the opening 36 of the injection tip 16. Further, the lower end surface of the second cylindrical portion 46, which is increased in diameter from the first cylindrical portion 45, on the first cylindrical portion 45 side is a step portion 51 that rises from the first cylindrical portion 45 in the radial direction of the first cylindrical portion 45. Accordingly, when the insertion portion 50 is inserted in the reservoir 31, the insertion of the insertion portion 50 with respect to the reservoir 31 is restricted by the step portion 51 abutting against the upper end surface of the reservoir 31. An opening 54 that opens the internal space of the second cylindrical portion 46 upward (to the side opposite to the blade portion 44) is formed at the upper end of the second cylindrical portion 46. The opening 54 is an opening into which the pipette head 3 is inserted so that the piercing tip 15 is mounted onto the pipette head 3 (see FIG. 17).

As illustrated in FIGS. 2 and 6 to 9, the flange portion 47 is a part that is locked to the first storage well 14A. The flange portion 47 extends radially outward of the second cylindrical portion 46 in the upper end portion of the second cylindrical portion 46. Further, the flange portion 47 is locked by a step-shaped locking portion 18A formed in the first storage well 14A when the piercing tip 15 is stored in the first storage well 14A of the reagent cartridge 1. The position of the locking portion 18A can be a position where the piercing tip 15 does not reach the bottom surface of the first storage well 14A and the upper end of the piercing tip 15 is lower than the upper end of the first storage well 14A when the flange portion 47 is locked.

As illustrated in FIGS. 6 to 13, the piercing tip 15 has one or a plurality of protrusions 52 and one or a plurality of grooves 53.

The protrusion 52 is a part that functions as a fitting portion fitted to the injection tip 16 and connecting the injection tip 16 and the piercing tip 15. The protrusion 52 is formed so as to protrude from the outer peripheral surface of the first cylindrical portion 45. Further, when the insertion portion 50 is inserted in the reservoir 31, the protrusion 52 is fitted to the injection tip 16 by being pressed against the inner peripheral surface of the reservoir 31. In addition, the protrusion 52 is formed at a position corresponding to the groove 39 when the insertion portion 50 is inserted in the reservoir 31 and the step portion 51 abuts against the upper end surface of the reservoir 31. Accordingly, when the insertion portion 50 is inserted in the reservoir 31, the protrusion 52 is fitted to the injection tip 16 also by fitting into the groove 39 formed in the inner peripheral surface of the cylindrical portion 33.

Although the shape of the protrusion 52 is not particularly limited, it is preferable that the protrusion 52 is triangular or the like and has an inclined surface in which the protrusion height from the first cylindrical portion 45 gradually increases from the lower end side toward the upper end side. The number of the protrusions 52, which is not particularly limited, is preferably two or more. In a case where the plurality of protrusions 52 are formed on the piercing tip 15, it is preferable that the plurality of protrusions 52 are positioned at equal intervals in the circumferential direction of the first cylindrical portion 45. In addition, in a case where the plurality of protrusions 52 are formed on the piercing tip 15, the number of the protrusions 52 can be, for example, four without being particularly limited.

The groove 53 is a part that functions as an air vent allowing the internal space A of the reservoir 31 to be ventilated from the outside in a state where the injection tip 16 and the piercing tip 15 are connected. The groove 53 is configured by a groove portion 53A formed in the outer peripheral surface of the first cylindrical portion 45 and a groove portion 53B formed in the step portion 51. The groove portion 53A formed in the first cylindrical portion 45 and the groove portion 53B formed in the step portion 51 constitute one groove 53 by communicating with each other. The groove portion 53A formed in the first cylindrical portion 45 extends from the recess 49 of the blade portion 44 to the step portion 51. The groove portion 53B formed in the step portion 51 extends from the groove 53 formed in the first cylindrical portion 45 to the outer peripheral surface of the second cylindrical portion 46.

The shape of the groove portion 53A formed in the first cylindrical portion 45 is not particularly limited. The groove portion 53A can be, for example, a groove having an arcuate cross section and extending in the direction that is parallel to the axis of the first cylindrical portion 45 from the viewpoint of manufacturing facilitation or the like. In addition, the groove portion 53B formed in the step portion 51, which is not particularly limited, can be a groove having an arcuate cross section and extending in the radial direction of the first cylindrical portion 45 from the viewpoint of manufacturing facilitation or the like. The number of the grooves 53, which is not particularly limited, is preferably two or more. In a case where the plurality of grooves 53 are formed in the piercing tip 15, it is preferable that the plurality of grooves 53 are positioned at equal intervals in the circumferential direction of the first cylindrical portion 45. In addition, in a case where the plurality of grooves 53 are formed in the piercing tip 15, the number of the grooves 53 can be, for example, four without being particularly limited.

Polypropylene or the like can be used as the material of the piercing tip 15, which is not particularly limited.

[Genetic Testing Method]

Next, a genetic testing method using the genetic testing device will be described.

First, the reagent cartridge 1, the microchip 2, and a reaction tube 4 (see FIG. 18) are set in the genetic testing device.

Figure 17:
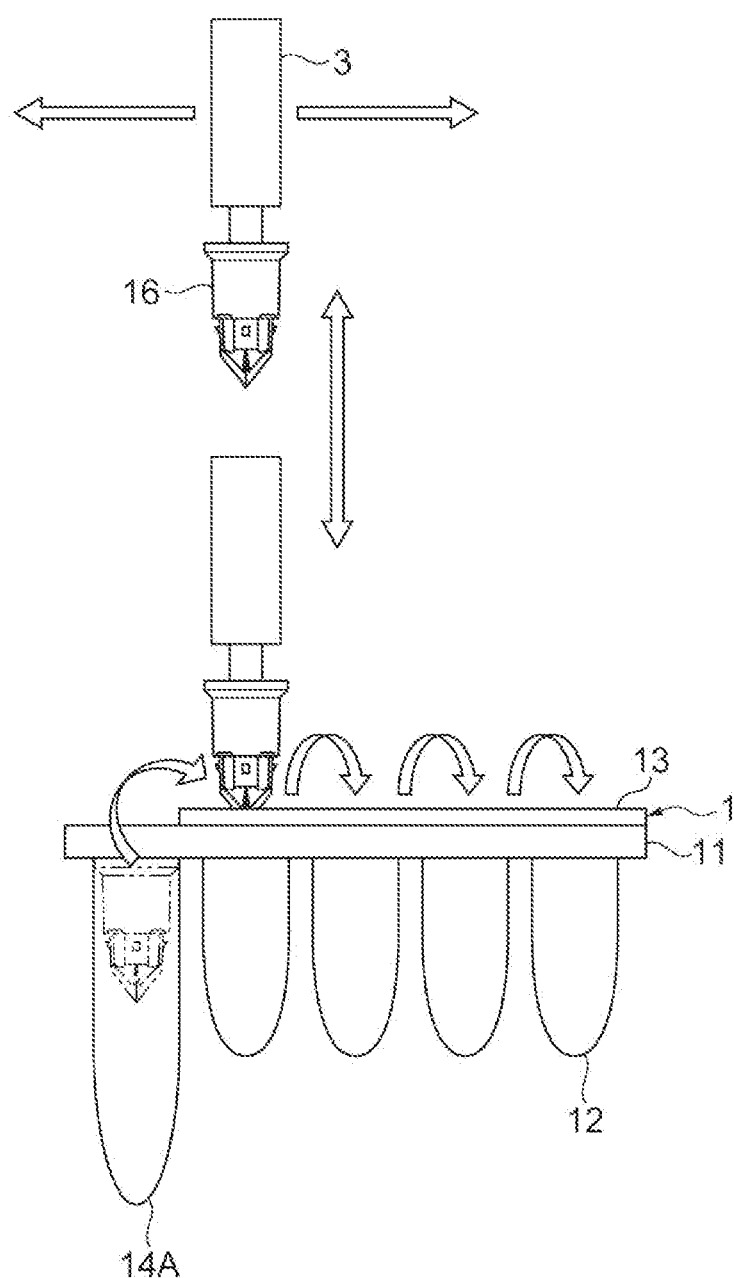
FIG. 17 is a schematic diagram for describing a genetic testing method.

Next, as illustrated in FIG. 17, the piercing tip 15 is mounted onto the pipette head 3 by the pipette head 3 being inserted into the piercing tip 15 stored in the first storage well 14A. Then, with the piercing tip 15 mounted, the pipette head 3 is moved in the up-down and horizontal directions. As a result, the lid portion 13 of the reagent container 12 filled with the reagent is broken by the pipette head 3 and the reagent container 12 is opened. Then, the piercing tip 15 is removed from the pipette head 3 and the piercing tip 15 removed from the pipette head 3 is collected in the first storage well 14A.

Figure 18:
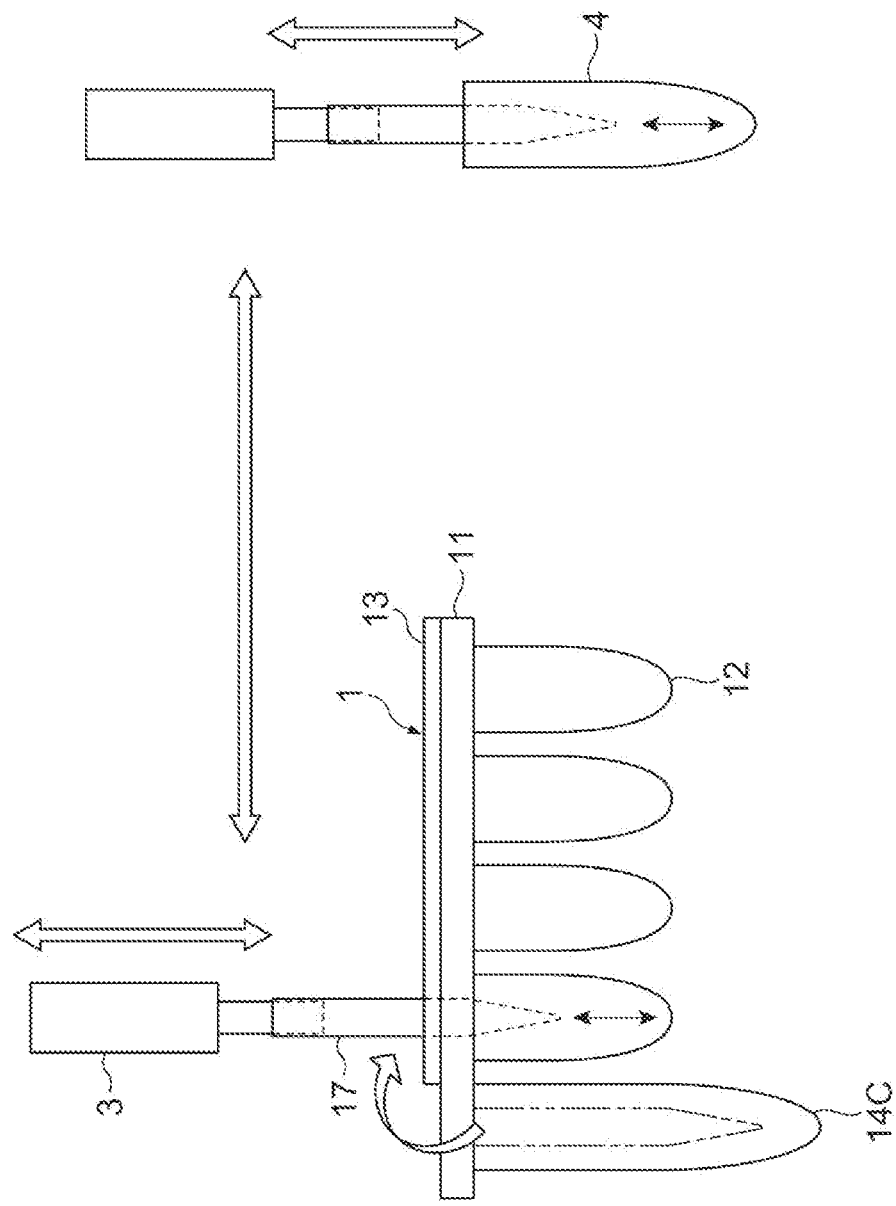
FIG. 18 is a schematic diagram for describing the genetic testing method.

Next, as illustrated in FIG. 18, the pipette tip 17 is mounted onto the pipette head 3 by the pipette head 3 being inserted into the pipette tip 17 stored in the third storage well 14C. Then, with the pipette tip 17 mounted, the pipette head 3 is moved in the up-down and horizontal directions. As a result, each reagent with which the reagent container 12 is filled is dispensed into the reaction tube 4 by the pipette tip 17. Then, the sample solution from which the target gene nucleic acid has been extracted and purified is prepared in the reaction tube 4 (extraction and purification step).

Figure 19:
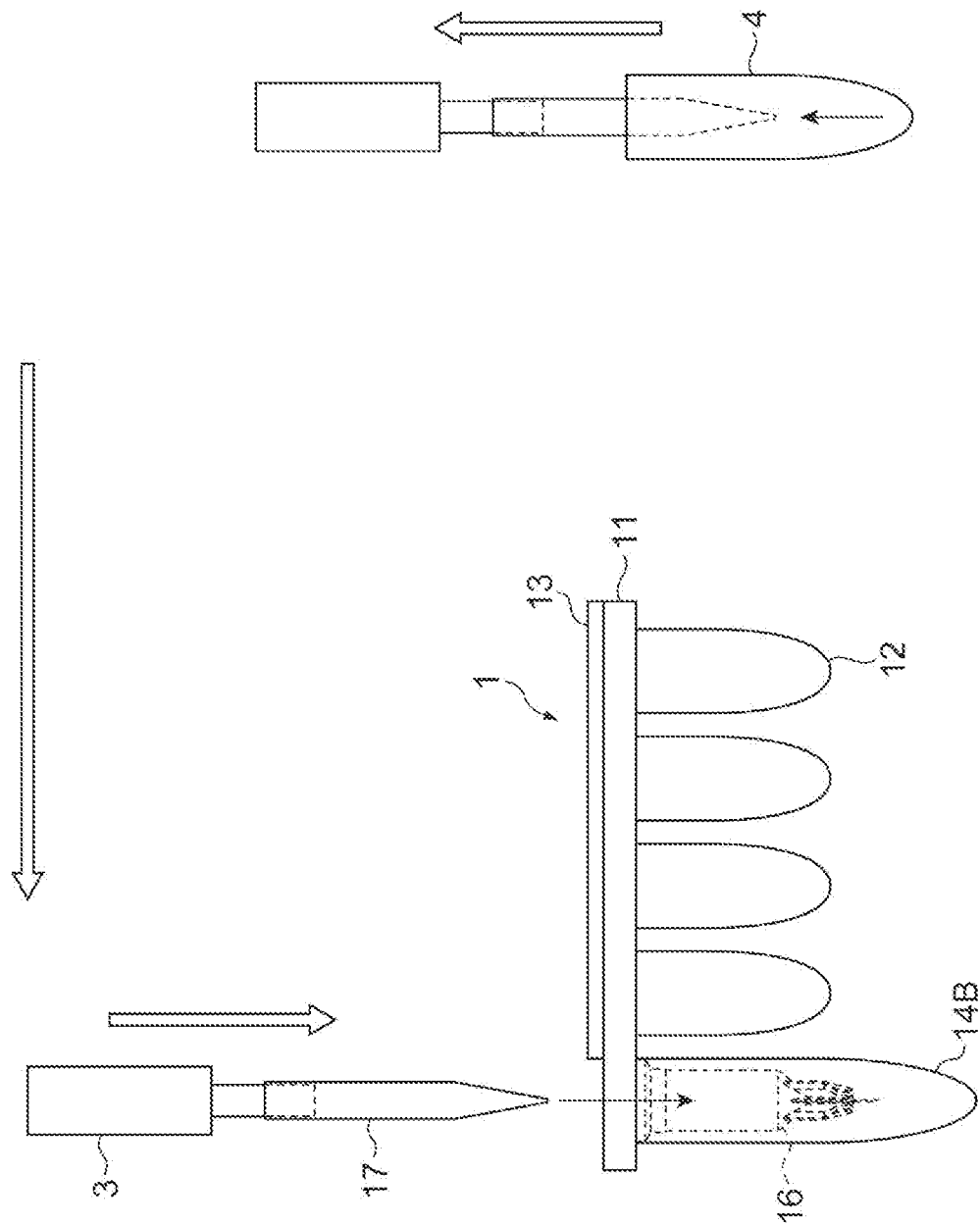
FIG. 19 is a schematic diagram for describing the genetic testing method.

Next, as illustrated in FIG. 19, the pipette head 3 is moved in the up-down and horizontal directions with the pipette tip 17 mounted. As a result, the sample solution prepared in the reaction tube 4 is dripped by the pipette tip 17 into the reservoir 31 of the injection tip 16 stored in the second storage well 14B. As a result, the sample solution is stored in the internal space A of the reservoir 31. Then, the pipette tip 17 is removed from the pipette head 3 and the pipette tip 17 removed from the pipette head 3 is collected in the third storage well 14C.

Figure 20:
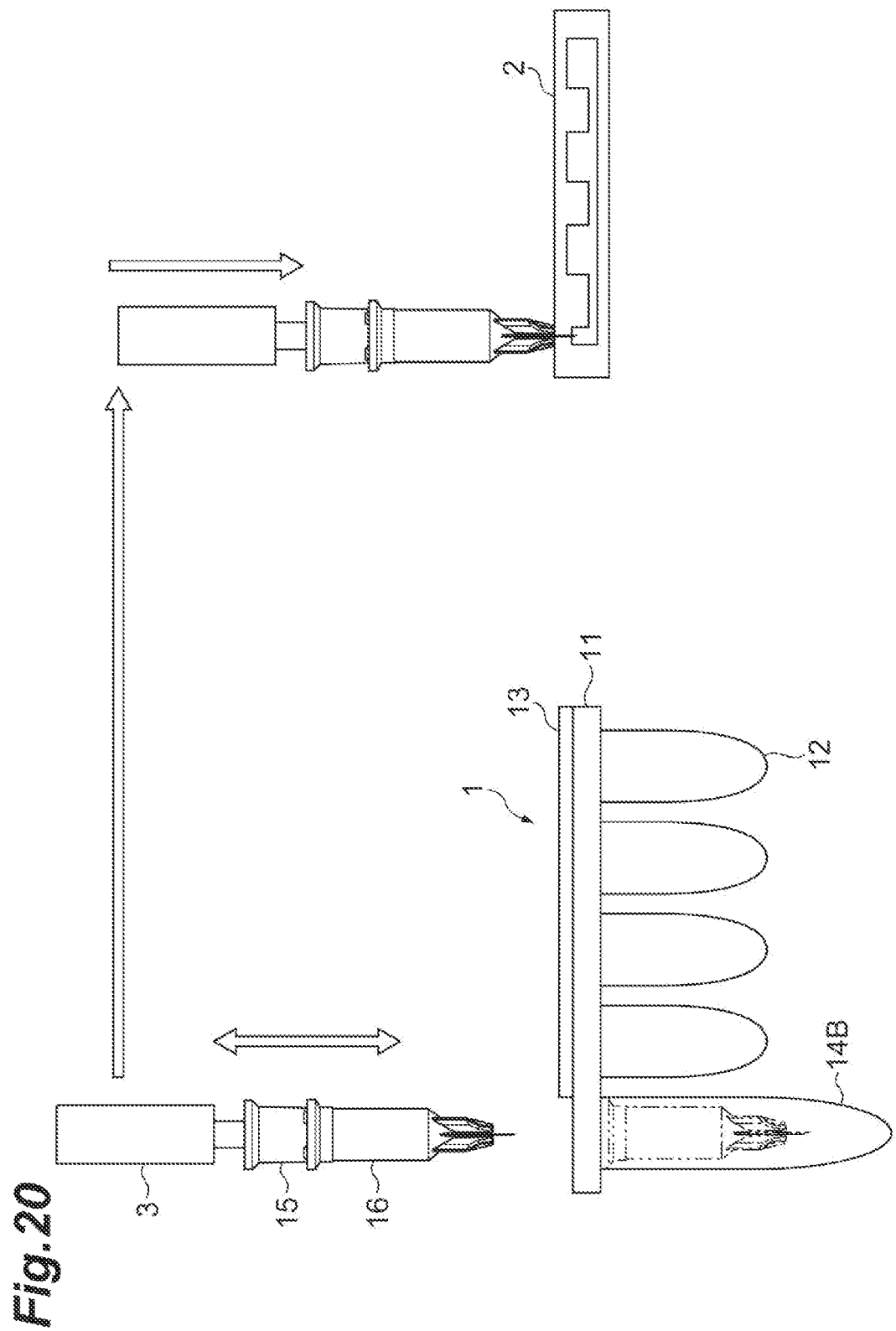
FIG. 20 is a schematic diagram for describing the genetic testing method.

Next, as illustrated in FIG. 20, the piercing tip 15 is mounted onto the pipette head 3 by the pipette head 3 being inserted into the piercing tip 15 stored in the first storage well 14A. Further, the injection tip 16 is mounted onto the pipette head 3 via the piercing tip 15 by the piercing tip 15 mounted on the pipette head 3 being inserted into the injection tip 16 stored in the second storage well 14B. As a result, the injection tip 16 and the piercing tip 15 are connected and the connected body is mounted onto the pipette head 3. Then, with the injection tip 16 mounted via the piercing tip 15, the pipette head 3 is moved in the up-down and horizontal directions. As a result, the sample solution is injected into the microchip 2 by the injection tip 16.

During the sample solution injection into the microchip 2, first, the injection needle 32 of the injection tip 16 punctures the confirmation space 24 of the microchip 2. Then, a very small amount of the sample solution is suctioned into the confirmation space 24 from the injection needle 32 by the negative pressure of the confirmation space 24. After it is subsequently confirmed that the sample solution has been suctioned into the confirmation space 24, the injection needle 32 of the injection tip 16 punctures the injection space 23a of the microchip 2. Then, the sample solution is suctioned from the injection needle 32 into the injection space 23a by the negative pressure of the reaction space 23. Then, spreading occurs from the injection space 23a to every reagent-enclosed space 23b along the flow path 23c and a reagent 5 enclosed in the reagent-enclosed space 23b is mixed with the sample solution. Then, the connected body of the injection tip 16 and the piercing tip 15 is removed from the pipette head 3 and the connected body removed from the pipette head 3 is collected in the second storage well 14B. At this time, the locking portion 18B of the second storage well 14B locks the flange portion 34 of the injection tip 16 such that the upper end of the injection tip 16 is sufficiently lower than the upper end of the second storage well 14B. Accordingly, the second storage well 14B is capable of storing the connected body of the injection tip 16 and the piercing tip 15. In other words, the piercing tip 15 is stored in the space of the second storage well 14B formed above the injection tip 16 stored in the second storage well 14B.

Subsequently, the nucleic acid is amplified by the microchip 2 being incubated at a predetermined temperature. Then, the amplified nucleic acid is detected by the presence or absence of an amplification product being confirmed in the microchip 2.

As described above, in the tip set according to the present embodiment, the injection tip 16 and the piercing tip 15 are connected by the protrusion 52 of the piercing tip 15 being fitted to the injection tip 16. Accordingly, it is possible to mount the injection tip 16 onto the pipette head 3 via the piercing tip 15 by mounting the piercing tip 15 connected to the injection tip 16 onto the pipette head 3. As a result, the injection tip 16 and the pipette head 3 do not come into direct contact with each other, and thus sample solution adhesion to the pipette head 3 attributable to fluctuation of the liquid surface of the sample solution is suppressed. As a result, contamination of the sample solution can be prevented.

In addition, it is possible to block at least a part of the opening 36 by means of the piercing tip 15 by inserting the insertion portion 50 of the piercing tip 15 into the reservoir 31 from the opening 36 of the injection tip 16. Further, the injection tip 16 and the piercing tip 15 are connected with at least a part of the opening 36 blocked by the piercing tip 15 by the protrusion 52 of the piercing tip 15 being fitted to the injection tip 16. Accordingly, it is possible to suppress sample solution leakage from the reservoir 31. As a result, contamination of the sample solution can be further prevented.

In addition, the protrusion 52 is pressed against the inner peripheral surface of the reservoir 31 when the insertion portion 50 is inserted in the reservoir 31, and thus it is possible to easily connect the injection tip 16 and the piercing tip 15 simply by inserting the insertion portion 50 of the piercing tip 15 into the reservoir 31. In addition, since the protrusion 52 is pressed against the inner peripheral surface of the reservoir 31, the connection precision and the fitting strength of the injection tip 16 and the piercing tip 15 are improved.

By the way, it becomes difficult to inject the sample solution from the injection needle 32 into the microchip 2 due to the internal pressure of the reservoir 31 when the opening 36 of the injection tip 16 is completely blocked by the piercing tip 15. In a case where the sample solution is suctioned into the microchip 2 from the injection needle 32 by the negative pressure in the microchip 2, in particular, the effect of the internal pressure of the reservoir 31 becomes extremely large. In the present embodiment, the groove 53 allows the internal space A of the reservoir 31 to be ventilated from the outside in a state where the injection tip 16 and the piercing tip 15 are connected, and thus the effect of the internal pressure of the reservoir 31 during sample solution injection from the injection needle 32 into the microchip 2 can be reduced. Accordingly, it is possible to appropriately inject the sample solution from the injection needle 32 into the microchip 2 even when the insertion portion 50 is inserted in the reservoir 31 from the opening 36 and the injection tip 16 and the piercing tip 15 are connected.

In addition, the groove 53 formed in the outer peripheral surface of the piercing tip 15 communicates with the internal space A of the reservoir 31, and thus the internal space A of the reservoir 31 can be opened to the atmosphere when the injection tip 16 and the piercing tip 15 are connected. As a result, an increase in the internal pressure of the internal space A is eliminated and it is possible to prevent the reagent solution from leaking out from the injection needle 32 in connecting the injection tip 16 and the piercing tip 15. Further, the effect of the internal pressure of the reservoir 31 during sample solution injection from the injection needle 32 into the microchip 2 can be extremely reduced.

In addition, the end surface of the reservoir 31 that is on the opening 36 side abuts against the step portion 51 of the piercing tip 15, and thus it is possible to restrict the amount of insertion of the piercing tip 15 with respect to the reservoir 31. As a result, when the injection tip 16 is mounted on the pipette head 3 via the piercing tip 15, the position of the injection tip 16 in the up-down direction can be positioned with high precision. In addition, since the groove 53 is also formed in the step portion 51, the internal space A of the reservoir 31 can be opened to the atmosphere even when the end surface of the reservoir 31 on the opening 36 side abuts against the step portion 51 of the piercing tip 15.

In addition, the piercing tip 15 has the blade portion 44 having a sharp tip, and thus the lid portion 13 of the reagent container 12 can be broken by the blade portion 44. Further, since the blade portion 44 has the plurality of blades 48 that radially extend and have a blade edge forming a polygonal pyramid ridgeline, the pressure by which the lid portion 13 of the reagent container 12 is broken is more concentrated than in a case where the blade portion is formed in a simple cone or polygonal pyramid. Accordingly, it is possible to break the lid portion 13 of the reagent container 12 with a smaller pressurizing force.

Although the embodiments of the present invention have been described above, the present invention is not limited to each above-described embodiment.

For example, although the protrusion 52 protruding from the outer peripheral surface of the insertion portion 50 is a fitting portion in the above-described embodiment, the fitting portion may be any configuration insofar as the fitting portion is capable of connecting the injection tip and the piercing tip by being fitted to the injection tip. For example, the fitting portion may be fitted to the injection tip over substantially the entire circumference of the second cylindrical portion with the outer shape of the second cylindrical portion being a truncated cone shape.

Figure 21:
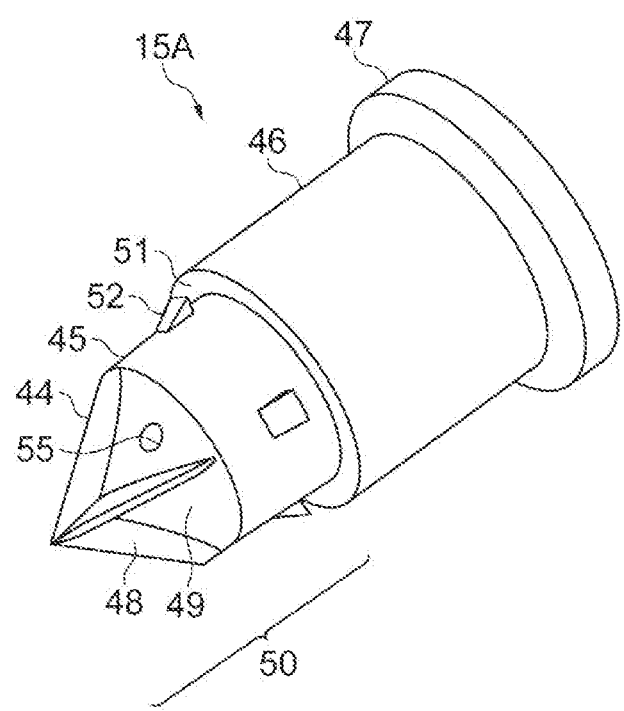
FIG. 21 a perspective view illustrating a piercing tip of a modification example.
Figure 22A:
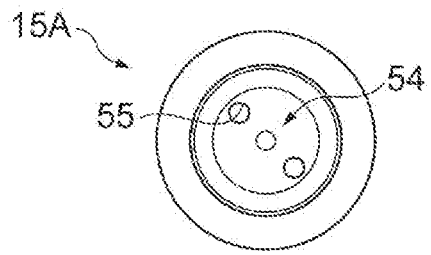
FIG. 22(a) is a plan view illustrating the piercing tip of the modification example.
Figure 22B:
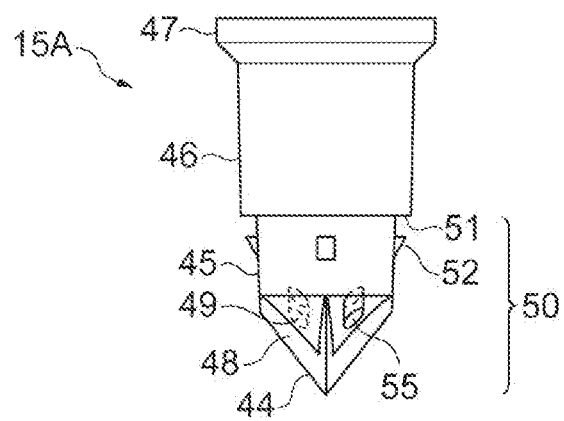
FIG. 22(b) is a front view illustrating the piercing tip of the modification example.
Figure 22C:
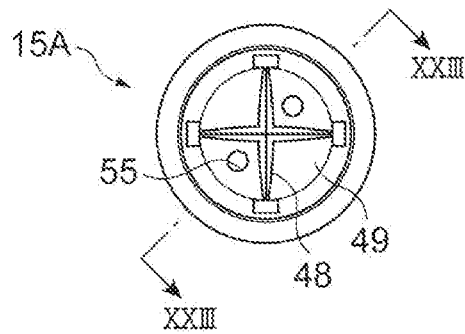
FIG. 22(c) is a bottom view illustrating the piercing tip of the modification example.
Figure 23:
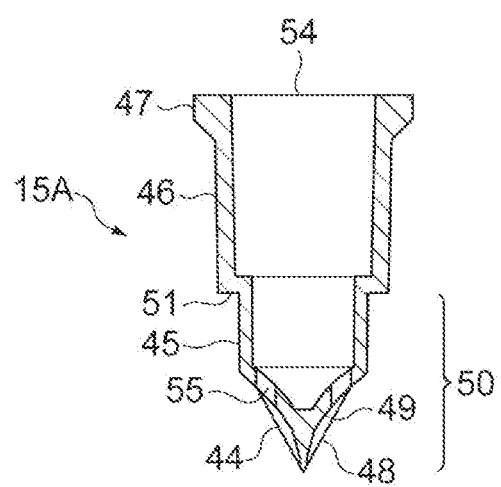
FIG. 23 is a cross-sectional view taken along line XXIII-XXIII illustrated in FIG. 22(c).

In addition, although the groove 53 formed in the outer peripheral surface of the piercing tip 15 is an air vent in the above-described embodiment, the air vent may be any configuration insofar as the internal space of the reservoir can be ventilated from the outside in a state where the injection tip and the piercing tip are connected. For example, the internal space of the reservoir may be ventilated from the outside via a through hole 55 with the through hole 55, which penetrates the blade portion 44, formed in the recess 49 as in a piercing tip 15A illustrated in FIGS. 21 to 23. In this case, the internal space of the reservoir can be ventilated from the internal space of the piercing tip 15A in a state where the injection tip and the piercing tip are connected.

In addition, although the groove 53 functioning as an air vent is configured by the groove portion 53A formed in the outer peripheral surface of the first cylindrical portion 45 and the groove portion 53B formed in the step portion 51 in the above-described embodiment, the groove portion formed in the outer peripheral surface of the first cylindrical portion may be the only groove functioning as an air vent in, for example, a case where no such step portion is provided or a case where there is a space between the opening-side end surface of the reservoir and the step portion.

In addition, although the air vent is formed at the piercing tip in the above-described embodiment, the air vent may be formed at the injection tip. For example, a groove functioning as an air vent may be formed in the inner peripheral surface of the reservoir and the opening-side end surface of the reservoir.

REFERENCE SIGNS LIST

1: reagent cartridge, 2: microchip, 3: pipette head, 4: reaction tube, 5: reagent, 11: cartridge main body, 12: reagent container, 13: lid portion, 14: storage well, 14A: first storage well, 14B: second storage well, 14C: third storage well, 15: piercing tip, 15A: piercing tip, 16: injection tip, 17: pipette tip, 18A: locking portion, 18B: locking portion, 21: chip main body, 22: reinforcing film, 23: reaction space, 23a: injection space, 23b: reagent-enclosed space, 23c: flow path, 24: confirmation space, 25: reagent, 26: first plate-shaped portion, 26a: reaction space recess, 27: second plate-shaped portion, 27a: surface, 31: reservoir, 32: injection needle, 33: cylindrical portion, 34: flange portion, 35: holding portion, 36: opening, 37: holding hole, 38: rib, 39: groove, 41: bevel, 42: needle tube, 43: needle base, 44: blade portion, 45: first cylindrical portion, 46: second cylindrical portion, 47: flange portion, 48: blade, 49: recess, 50: insertion portion, 51: step portion, 52: protrusion (fitting portion), 53: groove (air vent), 53A: groove portion, 53B: groove portion, 54: opening, 55: through hole (air vent), A: internal space.

The invention claimed is:

1. A tip set used for a genetic testing device, the tip set comprising:
a piercing tip configured for breaking a lid portion of a reagent container filled with a reagent to open the reagent container; and
an injection tip configured for injecting a sample solution containing a target gene nucleic acid into a microchip, wherein
the injection tip has a reservoir storing the sample solution in an internal space and an injection needle protruding from the reservoir,
an opening for opening the internal space to a side opposite to the injection needle is formed in the reservoir,
the piercing tip has a fitting portion fitted to the injection tip to connect the injection tip and the piercing tip,
the piercing tip has an insertion portion inserted into the reservoir from the opening, and
the fitting portion is fitted to the injection tip when the insertion portion is inserted in the reservoir.

2. The tip set according to claim 1, wherein
the fitting portion is a protrusion protruding from an outer peripheral surface of the insertion portion, and
the protrusion is pressed against an inner peripheral surface of the reservoir when the insertion portion is inserted in the reservoir.

3. The tip set according to claim 2, wherein at least one of the piercing tip and the injection tip further has an air vent allowing the internal space of the reservoir to be ventilated from an outside in a state where the injection tip and the piercing tip are connected.

4. The tip set according to claim 3, wherein the air vent is a groove formed in an outer peripheral surface of the piercing tip.

5. The tip set according to claim 4, wherein
the piercing tip has a step portion against which an end surface of the reservoir on the opening side abuts, and
the groove is also formed in the step portion.

6. The tip set according to claim 1, wherein
the piercing tip has a blade portion having a sharp tip, and the blade portion has a plurality of blades radially extending and having a blade edge forming a polygonal pyramid ridgeline.

\* \* \* \* \*